United States Patent [19]

Berg et al.

[11] Patent Number: 4,650,247

[45] Date of Patent: Mar. 17, 1987

[54] ORTHOPEDIC INSTRUMENT HAVING RELATIVELY ADJUSTABLE SEAT SECTIONS

[76] Inventors: Joseph A. Berg, 33186 Robin Hood Dr., Coarsegold, Calif. 93614; Cliff Gieszl, 250 E. Telegraph Rd., Space 256, Fillmore, Calif. 93015; Lee R. Jones, 13687 Chase, Arleta, Calif. 91331; Leonard W. Hughes, 6566 Tyrone Ave., Van Nuys, Calif. 91401

[21] Appl. No.: 769,346

[22] Filed: Aug. 26, 1985

[51] Int. Cl.[4] ............................ A47C 3/22; A61B 5/10

[52] U.S. Cl. ..................................... 297/284; 128/774; 297/312; 297/313; 297/330

[58] Field of Search ......................... 297/284, 311-314, 297/330, 337, 338; 128/774, 782; 108/3

[56] References Cited

U.S. PATENT DOCUMENTS

| | | | |
|---|---|---|---|
| 42,279 | 4/1864 | Douglas | 108/8 |
| 619,768 | 2/1899 | Lewis, Jr. | 297/312 |
| 2,482,996 | 9/1949 | Ursby | 297/312 |
| 2,799,323 | 7/1957 | Berg | 297/312 |
| 4,541,668 | 9/1985 | Rouw | 297/312 X |

*Primary Examiner*—Kenneth J. Dorner
*Assistant Examiner*—Peter R. Brown
*Attorney, Agent, or Firm*—William P. Green

[57] ABSTRACT

A biophysiometer having two seat sections which support the right and left sides respectively of a person's body, and are adapted for relative vertical movement and relative tilting movement to positions displacing the two sides of the body relative to one another in a manner tending to correct an abnormal posture conditions or otherwise attain a desired treatment effect. The two seat sections are preferably supported by a balancing connection operatively interconnecting them in a relation in which downward movement of one of the sections causes upward movement of the other section, and vice-a-versa. Desirably, the apparatus includes automatic control means which respond to displacement of the two seat sections relative to one another by the weight or positioning of a person's body, and then automatically actuate the seat sections to changed relative positions tending to correct the posture or other abnormal condition sensed by the device.

28 Claims, 7 Drawing Figures

10
16
2
15
17
11
90
DISPLAY
PRINTER
89
23
22
COMPUTER
88
CONTROL
13
2
12
87
86

-15-
68

73
73
66
67
71
70
71a'
60
57
59
60
58
65

ORTHOPEDIC INSTRUMENT HAVING RELATIVELY ADJUSTABLE SEAT SECTIONS

This invention relates to an improved biophysiometer instrument to be utilized by persons in the healing arts for adjusting the relative orientation of different portions of a person's body.

BACKGROUND OF THE INVENTION

An instrument embodying the invention is of a known general type including a seat having two seat sections which support the right and left sides respectively of a person's body and are movable to change the positions of the two sides of the body relative to one another. Such devices have been used in the past for attempting to correct the posture of a person who may normally tend to sit in a position in which one side of the body is lower than the other or at a different inclination. The general procedure has been to first allow a patient to sit on the sectionally formed seat in the position which seems normal to him, following which an operator adjusts the two sections of the seat relative to one another until the proper orientation of the body is attained. The seat and patient are kept in this adjusted position for a short period of time on each treatment, in order to acquaint the patient with the proper posture and hopefully encourage maintenance of that posture after the treatment has been completed. In prior instruments of this type, one of the seat sections has been power actuable upwardly and downwardly relative to the other, and each of the seat sections has in addition been mounted for individual powered tilting movement in two different directions, to raise or lower the forward end of the seat section or raise or lower its outer edge relative to its inner edge. These various powered movements of the two seat sections have been attained by a motor having a series of sprocket type transmission assemblies adapted to be controllably and selectively connected to the motor to produce any desired type of movement under the control of a series of switches manually actuated by an operator.

SUMMARY OF THE INVENTION

The general purpose of the present invention is to provide improvements in instruments of the above discussed type, for enhancing the function of the apparatus and its salutary effect on the patient's body. Additionally, the invention introduces an automatic control of the mechanism enabling it to sense very precisely and reliably the extent to which the position of a user's body may vary from the optimum in the sitting position, and then automatically adjust the relatively movable seat sections to compensate for and correct the abnormal condition. The seat sections may be designed to shift relatively freely both vertically and in a tilting mode in conformance with the relative positioning of the right and left sides of a user's body when he or she initially sits on the instrument. Sensors then respond to the positions to which the two seat sections are displaced by the patient's body, and that information is utilized to drive a motor or motors for power actuating the sections to positions compensating for their initial displacement and tending to permanently correct the non-optimum posture condition. The compensating movement may be controlled by a computer appropriately programmed to determine the types of movement of the seat sections which will correct the unwanted posture.

The apparatus is desirably designed to allow for upward and downward movement of both seat sections, with these two sections preferably being joined by a balancing connection causing upward movement of one section in response to downward movement of the other section, and vice-a-versa. The balancing connection may be a parallelogram mechanism, which functions also to maintain the two seating sections in proper upwardly facing positions during their upward and downward movement. A single motor may operate the balancing connection and the two seat sections upwardly and downwardly.

Tilting movements of the two seat sections may be produced by two additional motors associated with the two seat sections respectively. Each of the three drives desirably has a lost motion characteristic, enabling the seat sections to be initially moved upwardly and downwardly and tilted by the user's body without corresponding movements of the motors, so that the sensors may first detect the positions of the right and left sides of the person's body before treatment and without interference or resistance by the motors, and then actuate the motors after such detection to forceably drive the seat sections in opposite compensating directions.

BRIEF DESCRIPTION OF THE DRAWINGS

The above and other features and objects of the invention will be better understood from the following detailed description of the typical embodiment illustrated in the accompanying drawings in which.

DESCRIPTION OF THE PREFERRED EMBODIMENT

Figure 1:
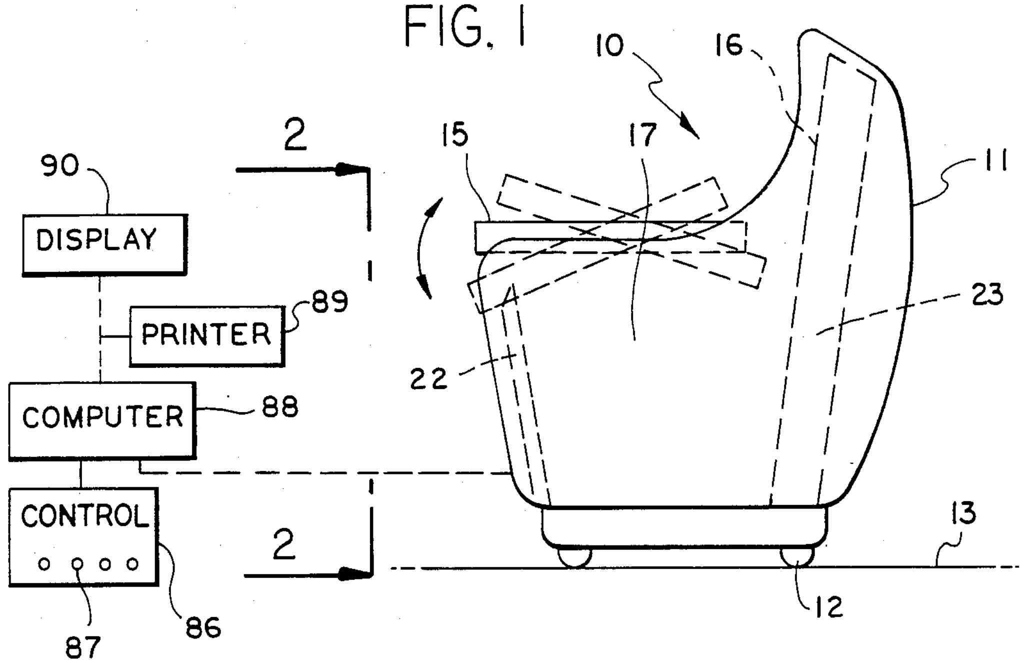
FIG. 1 is a side view of the biophysiometer of the invention.

The instrument 10 shown in the drawings includes a chair body 11 carrying casters 12 at its underside to support the instrument for movement to different locations along a floor surface 13. The chair body movably supports two right and left seat sections or plates 14 and 15 (FIG. 2) for engaging and supporting the right and left side of a person's body respectively. The chair includes an upwardly projecting back 16 for engaging and supporting the back of a user in sitting position, and has two vertically extending side walls 17 and 18 forming the opposite sides of a hollow compartment 19 beneath the seat sections within which the actuating mechanism 20 of the instrument is received. The compartment 19 may be closed at its bottom by a lower wall 21, and at the front and rear of mechanism 20 by a front wall 22 and a lower extension 23 of the seat back 16.

The two seat sections 14 and 15 may be identical and of rectangular horizontal section (see FIG. 3B), being spaced apart only very slightly at their inner closely proximate vertical parallel edges 24, and being somewhat elongated in a front to rear direction. These seat sections may have upper horizontal surfaces 25 which are aligned in a common horizontal plane in the normal position of the seat sections represented in full lines in FIGS. 1, 2 and 3. The seat sections are movable upwardly and downwardly between upper positions represented in broken lines at 14*a* and 15*a* in FIG. 2 and lower positions 14*b* and 15*b*. A balance arm structure 26 supports the seat sections 14 and 15 and interconnects them for coordinated but reverse movement so that when one of the sections moves upwardly from the full line normal position of FIG. 2 the other section moves downwardly from that level, and vice-a-versa. The balance mechanism 26 is in turn supported by a vertical support wall or frame member 27 which is rigidly secured to and projects upwardly from bottom wall 21, and may be appropriately braced to remain in fixed vertically extending condition by an angular bracket plate 28, with the elements 27 and 28 being typically attached to wall 21 by bolts or other fasteners represented at 29. The balancing mechanism 26 includes two identical upper horizontally extending levers or beams 30 at the front and back respectively of frame member 27 (see FIG. 3), with each of these beams being pivoted by a pin 31 (FIG. 2) to member 27 for pivotal movement about a horizontal axis 32 extending in a front to rear direction relative to the seat assembly. Mechanism 26 also includes two identical lower levers or beams 33 at the front and rear of member 27 (FIG. 3), each extending parallel to but spaced beneath the corresponding beam 30 and being pivoted to member 27 at 34 for pivotal movement about a horizontal axis 35 extending parallel to axis 32. The two upper beams 30 are pivotally connected at first ends 38 to upper portions of a vertical member 36, which is also pivotally connected at a lower point 39 to corresponding first ends of beams 33. The second ends of beams 30 and 33 are similarly connected pivotally at 38*a* and 39*a* to a second vertical member 37, with the axes of the four pivotal connections 38, 39, 38*a* and 39*a* being parallel to axes 33 and 35, so that the four elements 30, 33, 36 and 37 form a parallelogram mechanism acting to always maintain members 36 and 37 in directly vertical condition while allowing their upward and downward movement.

At their upper ends, the two vertical members 36 and 37 are connected to seat sections 14 and 15 to support the seat sections and move them upwardly and downwardly. The connection between each of the members 36 and 37 and the corresponding seat section includes a pivotal connection 138 or 139 mounting the seat section 14 or 15 for pivotal or tilting movement about a horizontal axis 40 or 41 relative to the connected element 36 or 37 to thereby allow each of the seat sections to swing or tilt about that axis 40 or 41 between the normal horizontal position represented in full lines in FIG. 3 and the broken line positions 15*c* and 15*d* (or 14*c* and 14*d*) in which the forward end of the seat section is tilted upwardly or downwardly relative to its rear end. Each of the pivotal connections 138 or 139 may include a horizontal projection 42 attached to and extending horizontally from the upper end of member 36 or 37 (see FIG. 3*a*), and into which two horizontally aligned bolts 46 are threadedly connected, with those bolts functioning as pivot pins and extending through aligned openings 146 in two downwardly projecting angle arms or brackets 44 and 45 attached rigidly to the underside of the corresponding seat section 14 or 15, to mount the section 14 or 15 for pivotal movement about the axis 40 or 41 of the bolts.

Figures 3, 3A, 3B:
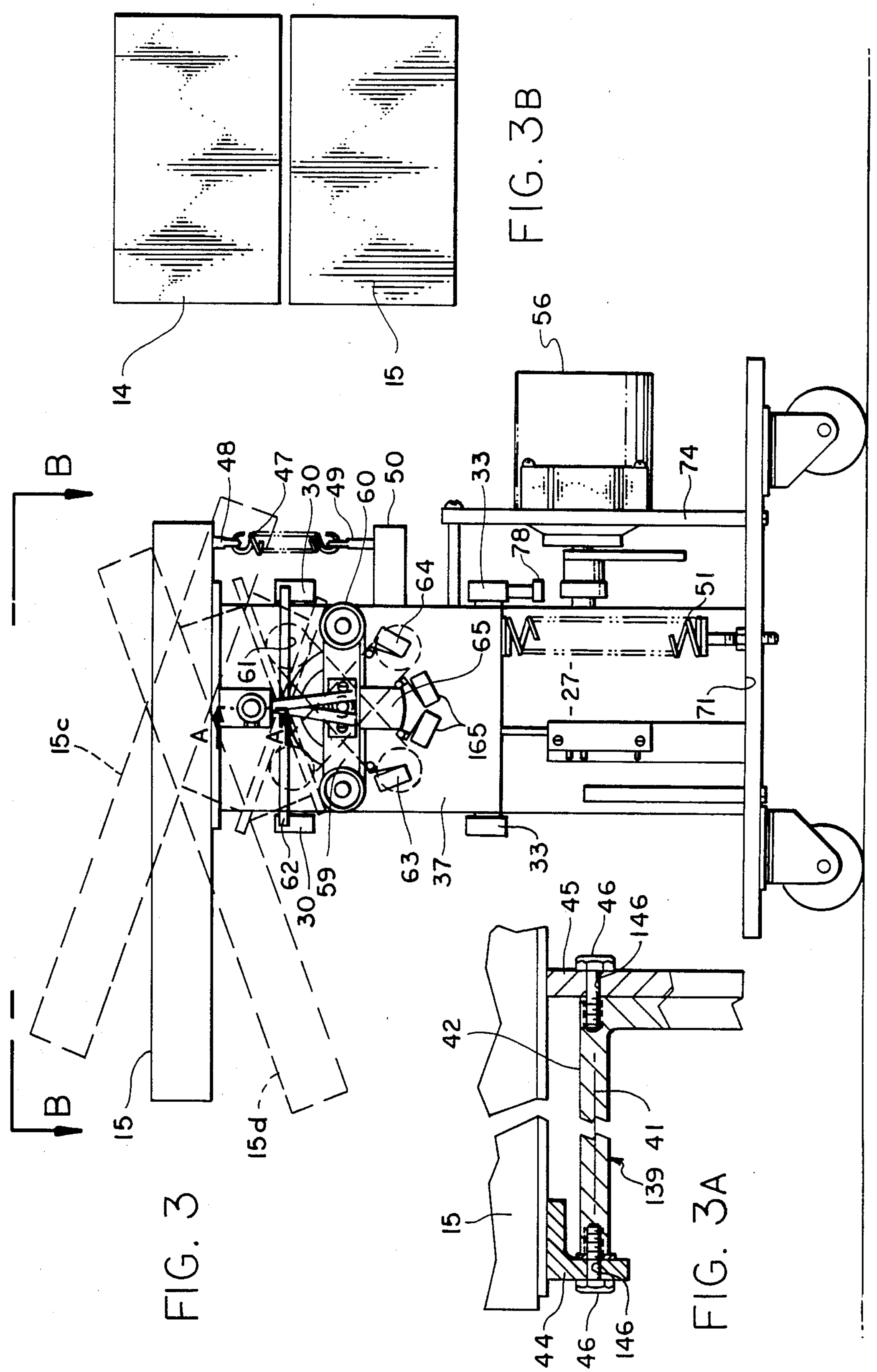
FIG. 3 is a vertical section taken on line 3—3 of FIG. 2, and showing the inner mechanism of the device.
FIG. 3*a* is an enlarged fragmentary vertical section taken on line A—A of FIG. 3.
FIG. 3*b* is a top plan view of the two seat sections taken on line B—B of FIG. 3.

Each of the seat sections may be yieldingly retained in the normal full line horizontally extending position of FIG. 3 by a vertically extending coil spring 47 connected at its upper end to an eye 48 attached to the underside of the rear portion of a corresponding one of the seat sections 14 or 15, and connected at its lower end to an eye 49 rigidly secured to a lug 50 projecting outwardly from and movable upwardly and downwardly with a corresponding one of the vertical members 36 or 37.

Figure 2:
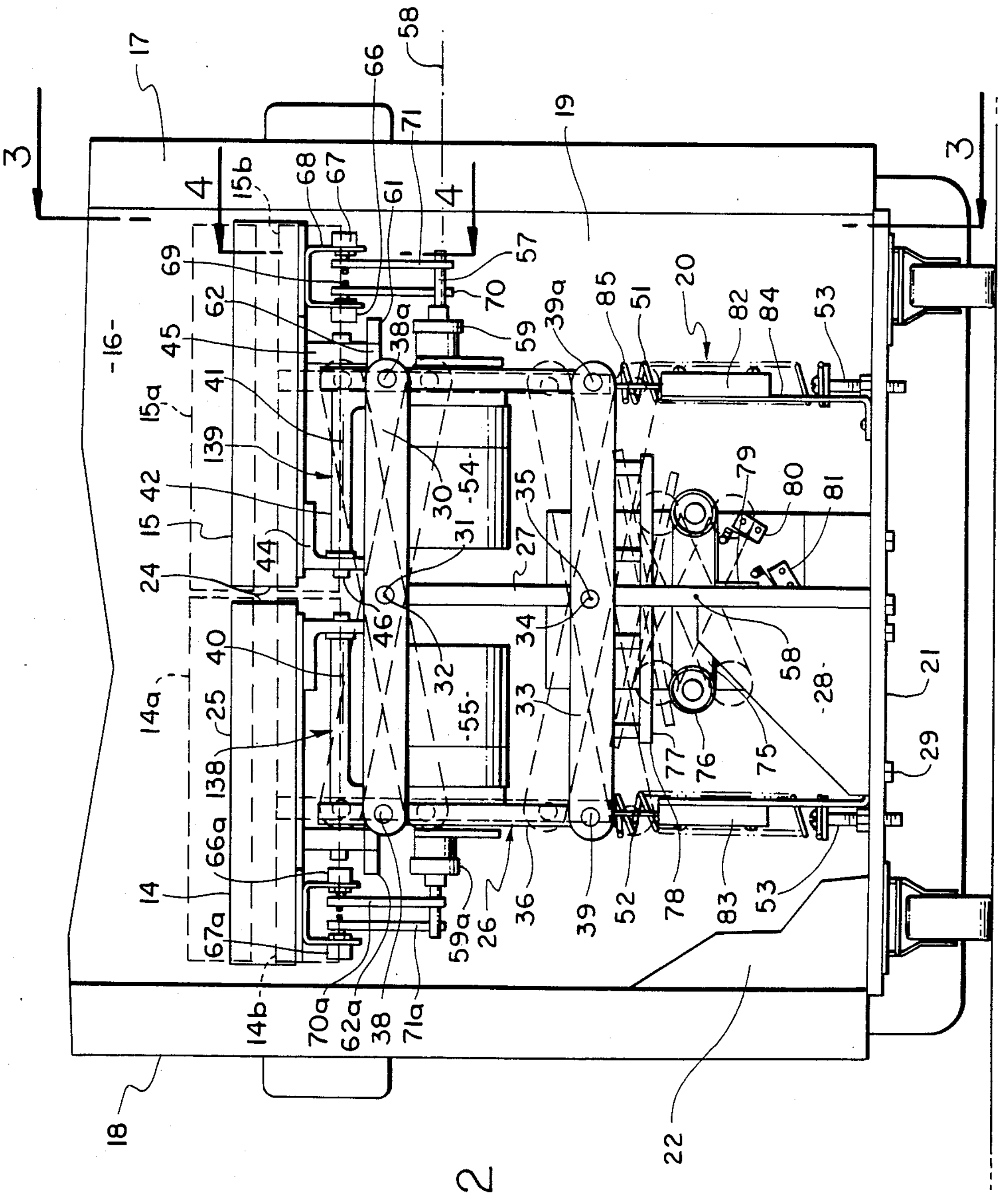
FIG. 2 is a fragmentary front view, partially broken away, taken on line 2—2 of FIG. 1.

Two additional springs 51 and 52, which may be identical with one another, yieldingly urge the balancing mechanism 26 to its normal position represented in full lines in FIG. 2. These springs are maintained under compression, and bear downwardly at their lower ends against bottom wall 21 of the instrument and upwardly at their upper ends against the two vertically extending and vertically movable members 36 and 37 of the balancing mechanism. The springs exactly balance one another in the normal positions of the seat sections represented in full lines in FIG. 2, to yieldingly maintain the seat sections in those positions, while permitting one of the seat sections to move downwardly with corresponding upward movement of the other section under the influence of uneven load forces produced by the right and left sides of a user's body. The compression of the two springs 51 and 52 may be adjusted by relative vertical adjustment of two members 53 which are threadedly connected to lower wall 21 of the instrument and against which the lower ends of springs 51 and 52 exert their downward force, so that by appropriate adjustment of these lower force transmitting elements 53 the seat sections can be aligned exactly horizontally in the normal conditions to which they tend to return when no one is sitting on sections 14 and 15.

Three electric motors 54, 55 and 56 act to control the three types of movement of the seat sections, with motor 54 controlling tilting action of seat section 15, motor 55 controlling the tilting of section 14, and with the balance motor 56 serving to control the actuation of balancing mechanism 26. These three motors 54, 55 and 56 may be identical, each being a digital step-by-step motor which can be controllably rotated to any desired setting in order to precisely position the seat sections as to tilt and balance. With reference first to motor 54, the housing of that motor is rigidly secured to the vertically extending member.37 at the underside of seat section 15, for movement upwardly and downwardly therewith. The output shaft 57 of motor 54 is driven about a horizontal axis 58 through an internal speed reducing transmission within the motor housing, and is appropriately attached rigidly to a horizontally extending member 59 (FIGS. 2, 3 and 4) having cam wheels or discs 60 at its opposite ends which are engageable upwardly against a normally horizontally extending planar undersurface 61 of a member 62 attached rigidly to the underside of the corresponding seat section, as by connection to the previously mentioned bracket element 45 secured to the seat section. Member 62 and its undersurface 61 are elongated horizontally in the same direction in which member 59 extends, with surface 61 being spaced upwardly above the level of the two cam elements 60 on the member 59 in the FIG. 4 condition of the parts to provide a lost motion connection between element 59 and member 62 and the seat section. Thus, the seat section 15 is free for tilting movement by the user's body between the two extreme positions represented in broken lines in FIG. 3 without contacting cam elements 60, and consequently without pivotal movement of member 59 and the output shaft of motor 54. However, if the motor is energized to swing member 59 from its normal horizontal condition of FIG. 3, one of the cams 60 will ultimately contact the undersurface 61 of member 62 carried by the seat section, to forceably pivot the seat section to any desired tilted condition.

The swinging movement of member 59 about its pivotal axis 58 is limited by actuation of two limit switches 63 and 64 which are carried by member 37 and are actuable by a member 65 which projects downwardly from and is rigidly secured to lever 59 and pivots therewith. When member 59 is swung about axis 58 to one of its two extreme positions (broken line positions of FIG. 3), projection 65 engages and actuates switch 63, which thus produces a signal acting to prevent further upward tilting movement of the forward end of the seat section. Similarly, in the opposite extreme position, projection 65 engages and actuates the other limit switch 64, to prevent further downward tilting movement of the forward end of the seat section. Two additional switches 165 are carried by member 37 at locations between the two switches 63 and 64, and are simultaneously actuated and closed by projection 65 in the normal horizontally extending position of member 59 represented in FIGS. 3 and 4, and act to control circuitry serving to maintain the lever in that centered normal horizontal condition.

The tilting movement of seat section 15 between its different settings of FIG. 3 is sensed by appropriate motion sensing means, preferably including two rotary potentiometers 66 and 67 whose housings are secured in fixed position relative to seat section 15 by a U-shaped mounting bracket 68 at the underside of the seat section, with the rotary shafts 69 of the two potentiometers turning about the pivotal axis 41 about which seat section 15 tilts. Two arms 70 and 71 are attached rigidly to the two rotary shafts 69 respectively of potentiometers 66 and 67, and have their lower ends received at opposites sides of and bearing inwardly against the output shaft 57 of motor 54. Two torsion springs 73 urge arms 70 and 71 inwardly against shaft 57.

Figure 4:
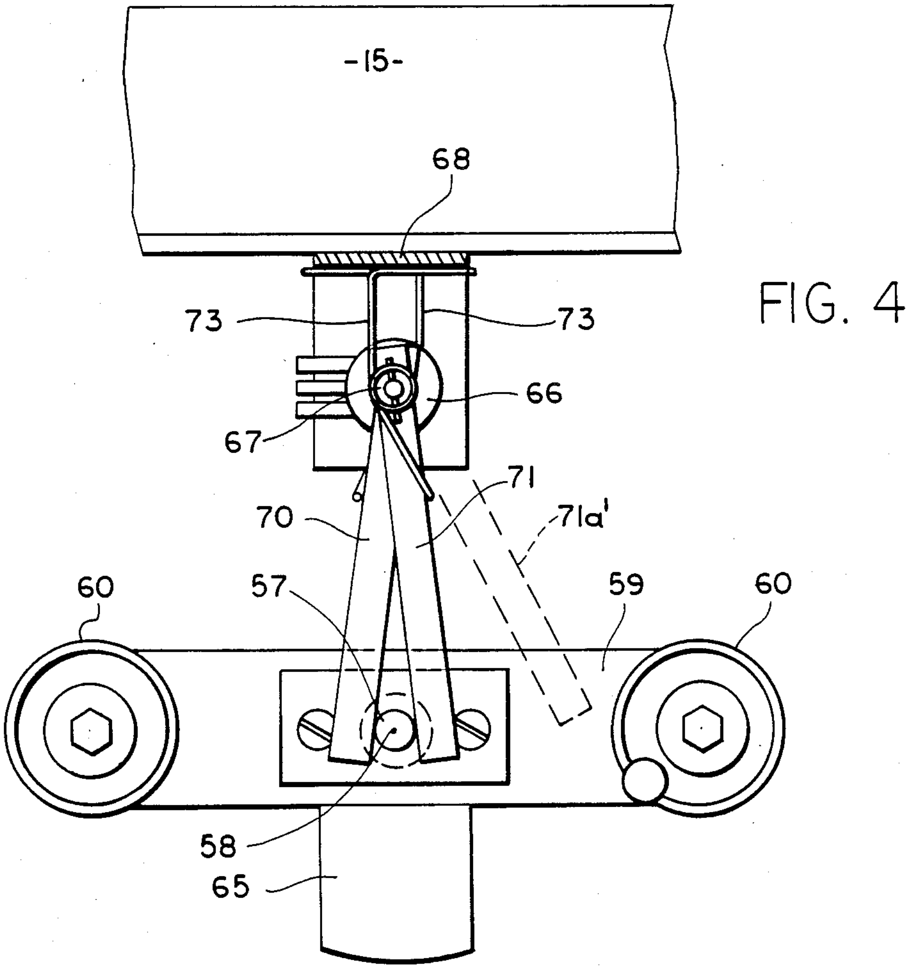
FIG. 4 is an enlarged fragmentary vertical section taken on line 4—4 of FIG. 2.

When the front of seat section 15 tilts downwardly, as to the broken line position **15*d* of FIG. 3, the housing of potentiometer 66 turns about axis 41 with the seat section, but the shaft 69 of that potentiometer is retained against such pivotal movement by virtue of the engagement of arm 70 connected to that shaft with the left side of shaft 57 as viewed in FIG. 4. Thus, potentiometer 66 is actuated to a setting in which it can regulate an output voltage to a value representing the direction of tilting movement of the seat section and proportional to the extent of that tilting movement. During that same tilting movement, the second arm 71 moves away from engagement with shaft 57, as to the position represented in broken lines at 71*a'* in FIG. 4. The internal stop of potentiometer 66 causes such swinging movement of arm 71 away from shaft 57. Similarly, upon tilting movement of seat section 15 in the opposite direction, arm 71 is retained by shaft 57 against pivotal movement with the seat section, while arm 70 swings leftwardly away from engagement with shaft 57, with the result that potentiometer 67 is actuated to a position representing the extent of upward tilting movement of the forward end of seat section 15. Thus, these two potentiometers produce and control voltage signals representing and proportional to the downward tilt and upward tilt respectively of the forward end of section 15**.

The motor 55 which controls upward and downward tilt of the right hand seat section 14 has associated with it a lost motion drive connection and tilt sensing means identical with those described in detail in connection with the left hand seat section 15, and including a horizontally elongated member **59*a* driven by the motor, a member 62*a* spaced thereabove and connected to the seat section for tilting movement therewith, and two rotary potentiometers 66*a* and 67*a* actuated by downwardly projecting arms 70*a* and 71*a*, all corresponding to the elements 59, 62, 66, 67, 70 and 71 and related parts of the left hand seat section, assembly. In addition, the assembly associated with seat section 14 includes limit switches corresponding to those represented at 63 and 64 in FIG. 3, centering switches corresponding to those represented at 165, and a projection corresponding to that represented at 65** for actuating the switches.

The third motor 56 has its housing rigidly attached to a vertical frame member 74, which is appropriately secured rigidly to bottom wall 21 and member 27. The output shaft of the motor is connected to and drives a horizontally elongated member 75 corresponding to element 59 and having camming rollers 76 as it opposite ends spaced beneath but engageable upwardly against a normally horizontally extending undersurface 77 of a structure 78 rigidly secured to and adapted to swing about axis 35 with one of the beams 33 of the balancing mechanism 26. Thus, the motor 56 has the same type of lost motion drive connection with respect to the balancing mechanism as has been discussed with respect to the tilting motors and their actuated parts. More particularly, the balancing mechanism can swing between the broken line positions represented in FIG. 2 without corresponding movement of member 75. However, upon energization of motor 56, the corresponding pivotal movement of member 75 causes one of the rollers 76 to move upwardly through a range of movement and ultimately engage the undersurface 77 of structure 78 and thereby cause forced pivotal deflection of the balancing mechanism, with resultant upward movement of one of the seat sections and corresponding downward movement of the other seat section. A projection 79 extending downwardly from member 75 and pivotable therewith is adapted to engage two limit switches 80 in the extreme positions of the member 75 (corresponding to limit switches 63 and 64 of FIG. 3), and two centering switches 81 in a normal position in which the two seat sections are horizontally aligned (corresponding to switches 55 of FIG. 3), to control the extreme positions and centered position of the balancing mechanism.

The tilting movement of the levers 33 and 34 is sensed by two linear potentiometers 82 and 83, whose housings are attached rigidly to the frame of the device by connection to upwardly projection brackets 84 secured to bottom wall 21, and whose linearly movable actuating elements 85 may be yieldingly urged upwardly relative to the housings of the potentiometers by internal springs in the potentiometers and engage the underside of opposite ends of one of the levers 33 to move upwardly and downwardly in correspondence therewith. Thus, the potentiometer 83 acts to sense upward movement of seat section 14 and produce an output voltage proportional thereto, while potentiometer 82 senses upward movement of seat section 15 and produces an output voltage proportional to that upward movement.

The operation of the above described instrument may be regulated by actuation of a control unit 86 (FIG. 1) having various switches 87 manually actuable by an operator to either set the apparatus for automatic operation by an appropriately programmed control computer 88 having a printer 89 and display 90 or by manual actuation of the switches of unit 86. A typical arrangement for the control circuit is illustrated diagrammatically in FIG. 5.

Figure 5:
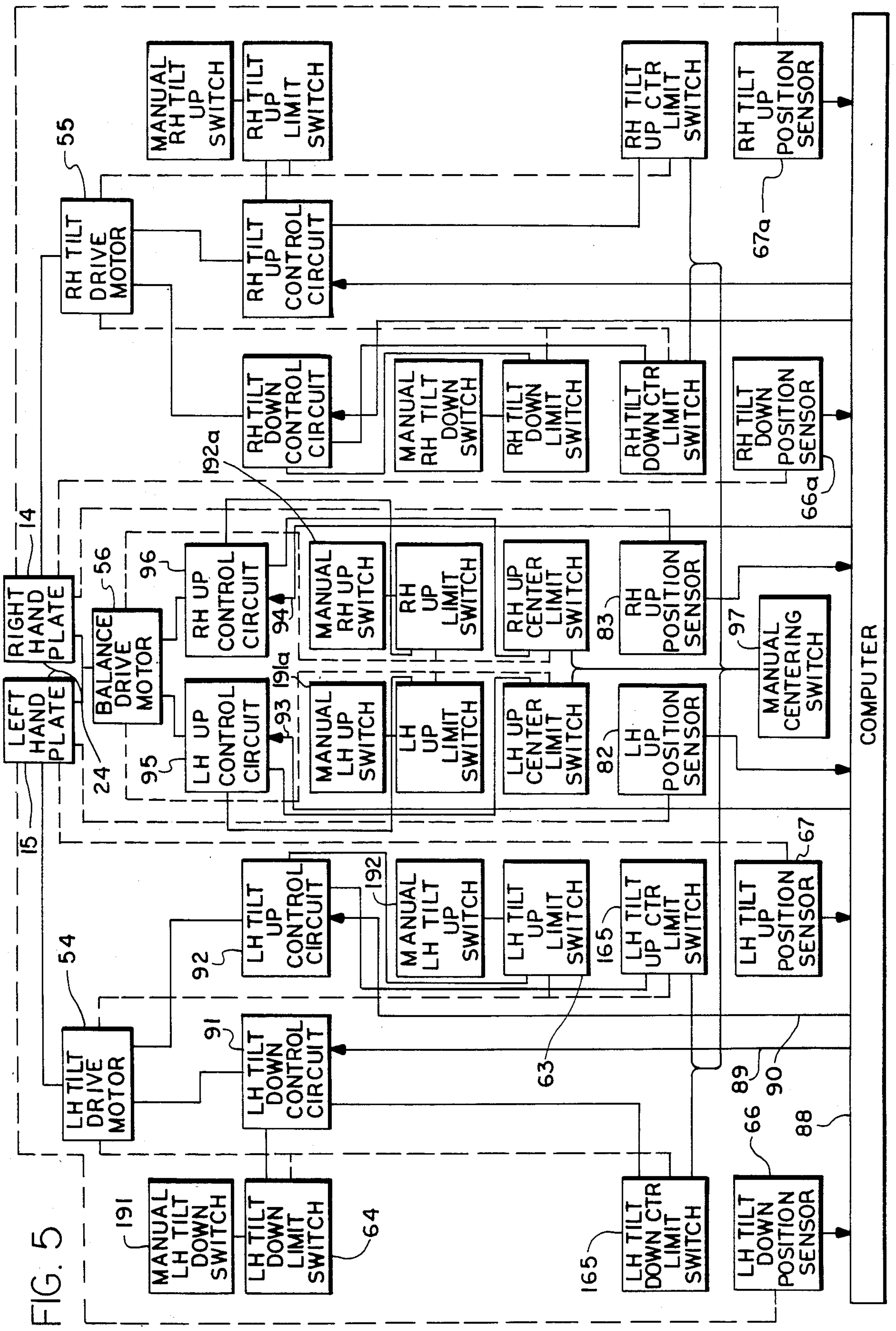
FIG. 5 is a schematic representation of the control circuitry for the instrument.

Referring to the left hand portion of the FIG. 5 circuit diagram, it is noted that the two tilt sensors 66 and 67 associated with left hand seat section 15 deliver their output signals to computer 88, to render the computer responsive to the extent of tilt of seat section 15. Similarly, the analogue voltage signals produced by the corresponding sensors **66*a* and 67*a* on the right hand seat section 14, representing the upward and downward tilt of that section, are delivered to the computer. In addition, the outputs from the sensors 82 and 83** representing the extent to which one of the seat sections may be above the level of the other seat section are delivered to the computer.

If the computer senses that the seat section 15 is tilted in either direction from its normal horizontally extending position represented in full lines in FIG. 3, the computer produces an output in one of the lines 89 or 90 causing a control circuit 91 or 92 to energize the reversible motor 54 to turn in a direction swinging member 59 pivotally. The direction in which the lever 59 swings is the opposite of the direction in which the seat section 15 has been pivoted by engagement with the user's body, to thus compensate for that pivotal movement. Preferably, the motor is actuated by the computer long enough to forceably swing the tilted seat section 15 back to its horizontal condition and through that condition to a position in which the seat is tilted in the opposite direction from that induced by the user's body, and through a number of degrees equalling the body induced deflection of the seat section. That is, if the forward end of seat section 15 is deflected downwardly through 15 degrees from the horizontal condition when a person sits on the device, the motor will automatically be actuated by the computer to swing the forward end of section 15 exactly 15 degrees beyond the horizontal, to introduce a compensating motion of the person's body acting to correct the improper posture. Similarly, if the forward end of the seat section is tilted upwardly by the person's body through a particular number of degrees, the computer will cause the motor to swing the section downwardly beyond the horizontal through that same number of degrees.

If either of the limit switches 63 or 64 is actuated, that switch delivers a signal to the corresponding control circuit 92 or 91 preventing further actuation of the motor and further pivotal movement of seat section 15. Similarly, the switches 165 provide signals to circuits 91 and 92 which automatically actuate the motor to a proper position for levelling the seat section 15 when a person is not present on the device. Manual control switches 191 and 192 can be set to bypass the computer and control the tilt of the seat manually if desired.

The operation of the circuitry shown in the right hand portion of FIG. 5 and associated with tilt motor 55 of the seat section 14 is identical with that described in connection with motor 54, and will not be discussed in detail.

Referring now to the central portion of FIG. 5, relating to balance drive motor 56, if one of the seat sections 14 or 15 is displaced downwardly lower than the other seat section when a person sits on the instrument, this condition is sensed by units 82 and 83, and the resultant analog voltage signals delivered to computer 88 by these sensors causes the computer to deliver an output through one of the lines 93 or 94 causing one of the control circuits 95 or 96 to energize balance motor 56 to turn in a direction to actuate sections 14 and 15 back toward their horizontally aligned conditions. Desirably, if the computer senses that section 14 has been lowered by engagement with a user's body a predetermined distance beneath section 15, the computer will cause circuit 96 to drive motor 56 to move section 14 upwardly through its normal position and to a position in which it is that same distance above section 15. Similarly, if the user's body moves section 15 downwardly through a particular distance beneath the level of section 14, the computer will desirably cause movement of section 15 upwardly to a location that same distance above section 14, to compensate for the initial abnormal orientation of the user's body in the same manner in which the tilting motors compensate for the tilting condition of the seat sections. The limit switches and centering switches function in conjunction with balance motor 56 in the same manner discussed in connection with tilt motor 54, and two manual control switches **191*a* and 192*a* can bypass the computer and actuate the seat sections upwardly and downwardly under manual control if desired. Also, a centering switch 97** is manually operable to return the seat sections to horizontally aligned normal positions when desired.

To recapitulate briefly the manner of use of the instrument, assume that the control circuitry has been set for automatic control, and that the seat sections are initially in horizontally extending condition and horizontally aligned with one another. When a person then sits on the two seat sections 14 and 15, one of those sections may move downwardly while the other moves upwardly in correspondence with the tendency of that person to apply more weight to one side of his body than the other, and similarly each of the seat sections may swing to a downwardly or upwardly tilted condition corresponding to the normal sitting posture of that person. The sensing potentiometers produce output voltages proportional in value to the extent and direction of vertical movement of the seat sections and tilting movement of the seat sections, and deliver those control signals to the computer, which then produces output signals as discussed acting to energize the motors digitally in a manner precisely rotating the output shafts of the motors and their driven members 59, **59*a* and 75**, so that each seat section is tilted in the reverse direction through the same number of degrees as it had been tilted by the person's body, and the seat section which was deflected by the body downwardly relative to the other is moved upwardly the same distance above the other section. The seat sections remain in this condition for a short period, say for example one or two minutes, enabling the patient to become accustomed to the changed orientation in a manner tending to cause the patient to assume a more correct posture after the treatment is over.

The display 90 gives the doctor and patient a visual indication at all times of the current condition of the apparatus, and printer 89 gives a complete permanent record of the initial deflection of the seat sections by the patient's body, the corrective movements caused by the computer, the times that movements are initiated and maintained, the patient's name, address, etc., and any other critical information which may be desired.

BEST AVAILABLE COPY

While a certain specific embodiment of the present invention has been disclosed as typical, the invention is of course not limited to this particular form, but rather is applicable broadly to all such variations as fall within the scope of the appended claims.

We claim:

1. A seat for aligning the right and left sides of a human body comprising:
   - two seat sections on which a person may sit with the right and left sides of the body supported by said sections respectively; and
   - a parallelogram mechanism having two generally horizontally extending upper and lower balance beams pivotally connected at corresponding approximately central locations for swinging movement in unison, and two generally vertically extending members supporting said two seat sections respectively and located near opposite ends respectively of said beams and each connected pivotally at vertically spaced locations to corresponding ends of the two beams so that downward movement of one seat section causes upward movement of the other seat section while the parallelogram mechanism maintains the seat sections in a desired upwardly facing orientation.

2. A seat as recited in claim 1, including two pivotal connections attaching said seat sections to said two generally vertically extending members respectively for independent relative pivotal movement about essentially horizontal axes to tilt the seat sections to differently inclined positions.

3. A seat for aligning the right and left sides of a human body comprising:
   - two seat sections on which a person may sit with the right and left sides of the body supported by said sections respectively;
   - a parallelogram mechanism having two generally horizontally extending upper and lower balance beams pivotally connected at corresponding approximately central locations for swinging movement in unison, and two generally vertically extending members supporting said two seat sections respectively and located near opposite ends respectively of said beams and each connected pivotally at vertically spaced locations to corresponding ends of the two beams so that downward movement of one seat section causes upward movement of the other seat section while the parallelogram mechanism maintains the seat sections in a desired upwardly facing orientation;
   - two pivotal connections attaching said seat sections to said two generally vertically extending members respectively for independent relative pivotal movement about essentially horizontal axes to tilt the seat sections to differently inclined positions; and
   - power operated means for swinging said balance beams to raise and lower said seat sections relative to one another, and for pivoting each of said seat sections independently to differently inclined positions.

4. A seat as recited in claim 3, in which said power operated means include a first motor for actuating said balance beams pivotally, and two additional motors for pivoting said two seats respectively to said inclined positions.

5. A seat as recited in claim 3, including means yieldingly urging said seat sections and said parallelogram mechanism to a predetermined normal position in which the two seat sections are at essentially the same level.

6. A seat as recited in claim 4, in which said parallelogram mechanism includes two additional upper and lower beams spaced from and pivoting in correspondence with said first mentioned upper and lower beams and connected pivotally at opposite ends to said generally vertically extending members.

7. A seat for aligning the right and left sides of a human body comprising:
   - two seat sections on which a person may sit and adapted to support the right side and left side respectively of the person's body;
   - means mounting at least one of said sections for movement relative to the other by the weight or positioning of the person's body when the posture of the body is incorrect;
   - power operated means for moving one section relative to the other to correct the posture; and
   - automatic control means responsive to movement of one of said sections relative to the other by a person's body to cause predetermined compensating movement of one of the sections relative to the other by said power operated means.

8. A seat as recited in claim 7, in which said automatic control means act upon movement of one of the sections in a first direction from a predetermined normal position to cause powered movement of the same section in the opposite direction from said normal position.

9. A seat as recited in claim 7, in which said automatic control means are constructed, in response to movement of one of said sections in a predetermined direction from a normal condition, to cause powered movement of the same section to the same extent in the opposite direction.

10. A seat as recited in claim 7, in which one of said seat sections is movable by the person's body and by said power operated means pivotally about an essentially horizontal axis to shift said one section to positions of varying inclination.

11. A seat as recited in claim 7, in which one of said sections is movable upwardly and downwardly relative to the other by a person's body and by said power operated means.

12. A seat as recited in claim 7, including means yieldingly urging said sections to predetermined normal positions.

13. A seat as recited in claim 7, in which said two seat sections are movable upwardly and downwardly relative to one another and are movable pivotally relative to one another about horizontal axes to differently inclined positions, by a person's body and by said power operated means, said automatic control means being responsive to relative vertical movement of the sections to cause compensating relative vertical movement of the sections by said power operated means, and being responsive to pivotal movement of either section by a person's body to cause compensating pivotal movement of the same section by said power operated means.

14. A seat as recited in claim 7, in which there is lost motion between said power operated means and a section actuated thereby to allow movement of said section by a person's body without corresponding movement of said power operated means.

15. A seat as recited in claim 7, in which there is lost motion between said power operated means and a seat section enabling movement of that seat section through a predetermined range by a person's body without cor-

BEST AVAILABLE COPY responding movement of said power operated means, said automatic control means including sensing means responsive to movement of said section within said range and acting to cause compensating movement in the opposite direction of the same section by said power operated means.

16. A seat as recited in claim 7, in which said power operated means includes an actuator driven pivotally about a predetermined essentially horizontal axis and acting to cause pivotal movement about a second essentially horizontal axis of one of said sections, there being a lost motion connection allowing pivotal movement of said seat section through a predetermined range without corresponding pivotal movement of said actuator.

17. A seat for aligning the right and left sides of a human body comprising:

two seat sections on which a person can sit with the right and left sides of the body supported by said sections respectively;

a balancing connection between said two seat sections mounting said sections for movement upwardly and downwardly relative to one another and operatively interconnecting the sections so that downward movement of one of said sections will cause upward movement of the other section, to support the two sides of the body at different levels;

means for sensing downward movement of one of said seat sections relative to the other seat section;

power operated seat actuating means; and automatic control means responsive to said sensing means upon said downward movement of one seat section relative to the other to cause said power operated means to effect predetermined compensating relative movement of the sections.

18. A seat for aligning the right and left sides of a human body comprising:

two seat sections on which a person can sit with the right and left sides of the body supported by said sections respectively;

a balancing connection between said two seat sections mounting said sections for movement upwardly and downwardly relative to one another and operatively interconnecting the sections so that downward movement of one of said sections will cause upward movement of the other section, to support the two sides of the body at different levels;

means for sensing downward movement of said one of said seat sections relative to the other;

power operated means for moving said sections upwardly and downwardly; and automatic control means responsive to said sensing means upon downward movement of said one section relative to the other to power actuate said one section in a reverse direction and upwardly relative to said other section.

19. A seat for aligning the right and left sides of a human body comprising:

two seat sections on which a person can sit with the right and left sides of the body supported by said sections respectively;

a balancing connection between said two seat sections mounting said sections for movement upwardly and downwardly relative to one another and operatively interconnecting the sections so that downward movement of one of said sections will cause upward movement of the other section, to support the two sides of the body at different levels;

power operated means for actuating said seat sections and said balancing connection to raise one of the sections and lower the other; and a lost motion connection between said power operated means and said sections and balancing connection in a relation allowing body weight-induced movement of said sections and balancing connection, caused by improper posture, without corresponding movement of said power operated means.

20. A seat for aligning the right and left sides of a human body comprising:

two seat sections on which a person can sit with the right and left sides of the body supported by said sections respectively;

a balancing connection between said two seat sections mounting said sections for movement upwardly and downwardly relative to one another and operatively interconnecting the sections so that downward movement of one of said sections will cause upward movement of the other sections, to supoort the two sides of the body at different levels;

said balancing connection including a balance beam structure connected near opposite ends thereof to said two seat sections respectively and mounted for pivotal movement at an intermediate location about a predetermined axis;

a motor; and an actuator driven pivotally about a second axis by said motor and adapted upon pivotal movement to engage said beam structure and displace it pivotally about said first axis;

there being lost motion between said actuator and said beam structure enabling said beam structure to be moved pivotally about said first axis through a range of movement by downward movement of one seat section relative to the other without corresponding pivotal movement of said actuator about said second axis.

21. A seat as recited in claim 20, including means for sensing the extent of pivotal movement of said beam structure about said first axis, and automatic control means responsive to said sensing means to energize said motor in a relation driving said actuator to engage said balance beam structure and displace it pivotally about said first axis in a direction the opposite of that sensed.

22. A seat as recited in claim 21, in which said automatic control means cause said motor to pivot said balance beam structure to an extent acting upon movement of one seat section a predetermined distance beneath the other section to power actuate said one section essentially that same distance above said other section.

23. A seat for aligning the right and left sides of a human body comprising:

two seat sections on which a person may sit and adapted to support the right side and left side respectively of the person's body;

a parallelogram mechanism including two vertically spaced balance beams mounted to swing in unison about two spaced axes, and including two structures carried by opposite ends of said balance beams for supporting the two seat sections respectively in a relation moving one of the seat sections upwardly in response to downward movement of the other section by a person's body;

two pivotal connections attaching said seat sections to said two last mentioned structures respectively for independent relative pivotal movement about essentially horizontal axes to tilt the seat sections, differently inclined positions;

power operated means for swinging said balance beams to raise and lower said seat sections relative to one another, and for pivoting each of said seat sections independently to differently inclined positions; and automatic control means responsive to relative vertical movement of said seat sections and to pivotal movement of either section to cause compensating movement of the sections or section by said power operated means.

24. A seat for aligning the right and left sides of a human body comprising:

two seat sections on which a person may sit and adapted to support the right side and left side respectively of the person's body;

a parallelogram mechanism including two vertically spaced balance beams mounted to swing in unison about two spaced axes, and including two structures carried by opposite ends of said balance beams for supporting the two seat sections respectively in a relation moving one of the seat sections upwardly in response to downward movement of the other section by a person's body;

two pivotal connections attaching said seat sections to said two last mentioned structures respectively for independent relative pivotal movement about essentially horizontal axes to tilt the seat sections to differently inclined positions; and power operated means for swinging said balance beams to raise and lower said seat sections relative to one another, and for pivoting each of said seat sections independently to differently inclined positions;

said balance beams being free for predetermined lost motion, and said seats being free for predetermined independent pivotal lost motion to differently inclined positions, without corresponding movement of said power operated means.

25. A seat for aligning the right and left sides of a human body comprising:

two seat sections on which a person may sit and adapted to support the right side and left side respectively of the person's body;

a parallelogram mechanism including two vertically spaced balance beams mounted to swing in unison about two spaced axes, and including two structures carried by opposite ends of said balance beams for supporting the two seat sections respectively in a relation moving one of the seat sections upwardly in response to downward movement of the other section by a person's body;

two pivotal connections attaching said seat sections to said two last mentioned structures respectively for independent relative pivotal movement about essentially horizontal axes to tilt the seat sections to differently inclined positions;

power operated means for swinging said balance beams to raise and lower said seat sections relative to one another, and for pivoting each of said seat sections independently to differently inclined positions;

means for sensing the extent of swinging movement of said balance beams and for sensing the extent of pivotal movement of each of said seat sections; and a computer responsive to said sensing means and acting to control said power operated means to compensate for body-induced movements of the seat sections caused by improper posture in accordance with a predetermined program.

26. A seat for aligning the right and left sides of a human body comprising:

two seat sections on which a person may sit and adapted to support the right side and left side respectively of the person's body;

a parallelogram mechanism including two vertically spaced balance beams mounted to swing in unison about two spaced axes, and including two structures carried by opposite ends of said balance beams for supporting the two seat sections respectively in a relation moving one of the seat sections upwardly in response to downward movement of the other section by a person's body;

two pivotal connections attaching said seat sections to said two last mentioned structures respectively for independent relative pivotal movement about essentially horizontal axes to tilt the seat sections to differently inclined positions;

power operated means for swinging said balance beams to raise and lower said seat sections relative to one another, and for pivoting each of said seat sections independently to differently inclined positions;

said power operated means including a first motor, a second motor, a third motor, a first actuator driven pivotally by said first motor and adapted to engage and pivotally displace said beams of said parallelogram mechanism and having a lost motion connection therewith enabling limited pivotal movement of the beams and relative vertical movement of the seat sections without corresponding movement of said first actuator, a second actuator driven by said second motor, a structure carried by a first of said seat sections and engageable by said second actuator to pivot the seat section and having lost motion with respect thereto enabling limited pivotal movement of said first seat section without corresponding movement of said second actuator, a third actuator driven pivotally by said third motor, and a structure carried by said second seat section and engageable by said third actuator to pivot the second seat section and having lost motion with respect to said third actuator to enable pivotal movement of said second seat section without corresponding movement of the third actuator.

27. A seat as recited in claim 26, including first sensing means for sensing pivotal movement of said balance beams, first automatic control means responsive to said first sensing means for energizing said first motor to pivot said first actuator to cause pivotal movement of said balance beams compensating for body-induced movement thereof sensed by said first sensing means, second sensing means for sensing body induced pivotal movement of said first seat section, automatic control means responsive to said second sensing means for energizing said second motor to cause powered compensating pivotal movement of said first section, third sensing means responsive to pivotal movement of said second seat section, and third automatic control means responsive to said third sensing means to energize said third motor to cause compensating pivotal movement of said second section.

28. A seat as recited in claim 27, including first balancing spring means acting against said balance beams to yieldingly urge them to a predetermined normal condition in which said seat sections are at a common level, second spring means yieldingly urging said first seat section to a normal essentially horizontally extending condition, and third spring means yieldingly urging said second seat section to a normal essentially horizontally extending condition.

* * * * *